(12) United States Patent
Soderman

(10) Patent No.: US 9,377,403 B2
(45) Date of Patent: Jun. 28, 2016

(54) ADAPTIVE LINEAR FILTER FOR REAL TIME NOISE REDUCTION IN SURFACE PLASMON RESONANCE SENSORGRAMS

(75) Inventor: Tobias Soderman, Uppsala (SE)

(73) Assignee: GE HEALTHCARE BIO-SCIENCES AB, Uppsala (JP)

( * ) Notice: Subject to any disclaimer, the term of this patent is extended or adjusted under 35 U.S.C. 154(b) by 682 days.

(21) Appl. No.: 13/637,389

(22) PCT Filed: Mar. 28, 2011

(86) PCT No.: PCT/SE2011/050340
§ 371 (c)(1),
(2), (4) Date: Sep. 26, 2012

(87) PCT Pub. No.: WO2011/123026
PCT Pub. Date: Oct. 6, 2011

(65) Prior Publication Data
US 2013/0016888 A1    Jan. 17, 2013

(30) Foreign Application Priority Data

Mar. 29, 2010   (SE) ...................................... 1050291

(51) Int. Cl.
*G01N 21/55*    (2014.01)
*G01N 21/552*   (2014.01)

(52) U.S. Cl.
CPC ..................................... *G01N 21/553* (2013.01)

(58) Field of Classification Search
CPC ....................................... G01N 21/553–21/554
See application file for complete search history.

(56) References Cited

U.S. PATENT DOCUMENTS

| 3,889,108 A | 6/1975 | Cantrell |
| 5,503,160 A | 4/1996 | Pering |
| 6,487,295 B1 | 11/2002 | Lofgren et al. |
| 7,230,714 B2 * | 6/2007 | Barford ................ G01N 21/553 356/445 |
| 8,045,173 B2 | 10/2011 | Chan |
| 8,155,906 B2 | 4/2012 | Andersson |
| 2006/0087656 A1 | 4/2006 | Barford et al. |

FOREIGN PATENT DOCUMENTS

| EP | 1 657 542 | 5/2006 |
| JP | 2004-037365 | 2/2004 |
| JP | 2005024456 | 1/2005 |
| WO | WO 03/081245 | 10/2003 |

* cited by examiner

*Primary Examiner* — Kara E Geisel
*Assistant Examiner* — Shawn Decenzo
(74) *Attorney, Agent, or Firm* — Sutherland Asbill & Brennan LLP

(57) ABSTRACT

A method for linear filtering of noise in a sensorgram generated from a surface plasmon resonance apparatus, the method comprising: providing a linear filter of variable length to filter an output signal in the sensorgram; and determining an optimal length of the linear filter based on a slope of the signal in the sensorgram and a locked interception linear error, LILE, detector.

20 Claims, 4 Drawing Sheets

United States Patent US 9,377,403 B2

ADAPTIVE LINEAR FILTER FOR REAL TIME NOISE REDUCTION IN SURFACE PLASMON RESONANCE SENSORGRAMS

BACKGROUND

The invention relates generally to a filtering scheme for noise reduction in Surface Plasmon Resonance (SPR) sensorgrams and more particularly, to an adaptive linear filtering scheme for noise reduction in SPR sensorgrams.

A surface plasmon resonance (SPR) measurement system typically presents detected changes in the refractive index of a sample in the form of a sensorgram. A sensorgram is a biomolecular interaction plot of the relative refractive index of the sample versus time and may contain one or more phases. Each phase of the plot includes a buffer-only period followed by association and dissociation periods. The association and dissociation periods include adsorption and desorption of biomolecules resulting in a change in refractive index. The adsorption-desorption can be followed in real-time and the amount of adsorbed species can be determined. The SPR sensorgrams may contain different types of noise components that can mask or otherwise distort features of the sensorgrams. The noise components may be attributed to measurement uncertainty in an optical apparatus of the SPR measurement system. The noise components may also be due to mechanical events such as the opening or closing of valves that control the flow of buffer and analytes in the samples. Furthermore, there may be drift in the measurements due to temperature variations or sample non-uniformities.

Various schemes have been investigated for noise reduction in SPR sensorgrams, including linear and nonlinear filtering. Linear filtering can be very effective in reducing random noise components present in a signal. However, convention linear filtering has been noted to have several shortcomings. When conventional linear filtering, such as lowpass filtering, is applied to an SPR sensorgram, high frequency features, such as sharp transitions in the sensorgram, may be smoothed out, or eliminated. Yet these sharp transitions may be indicative of a critical biochemical process or event, such as the onset of a binding event between analytes and ligands within the sample. Smoothing out or eliminating these sharp transitions can make determination of association/dissociation rates and other important indicators of biochemical processes more difficult or less accurate. Conventional linear filtering can also result in ringing when a signal includes discontinuities or other anomalies, making biochemical processes or events depicted in the SPR sensorgram difficult to interpret.

Therefore, it is desirable to have a linear filtering method for reducing noise while preserving important signal characteristics in SPR sensorgrams.

Sensorgram filtering is used to reduce high frequency noise that is random in its nature. E.g. air bubble outliers and steps should not be reduced due to filtering. Sensorgram filtering shall not affect kinetic constants.

BRIEF DESCRIPTION

In accordance with one embodiment of the invention, a method for linear filtering of noise in a SPR sensorgram generated from a surface plasmon resonance apparatus is provided. The method includes providing a linear filter of variable length to filter an output signal in the sensorgram. The method further includes determining an optimal length of the linear filter based on a slope of the signal in the sensorgram and locked interception linear error, LILE, detector. Thus, the method includes determining an adaptive filter length in real-time during measurement of refractive index in the apparatus for reducing noise in the sensorgram.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed in detail below, embodiments of the invention are directed towards an adaptive linear filtering method for noise reduction in SPR sensorgrams. The method includes providing a linear filter of variable length to filter an output signal in the sensorgram. As used herein, the term 'adaptive' refers to the dynamic variation of the linear filter length for ensuring that the output signal in the sensorgram is preserved.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Any examples of operating parameters are not exclusive of other parameters of the disclosed embodiments.

Figure 1:
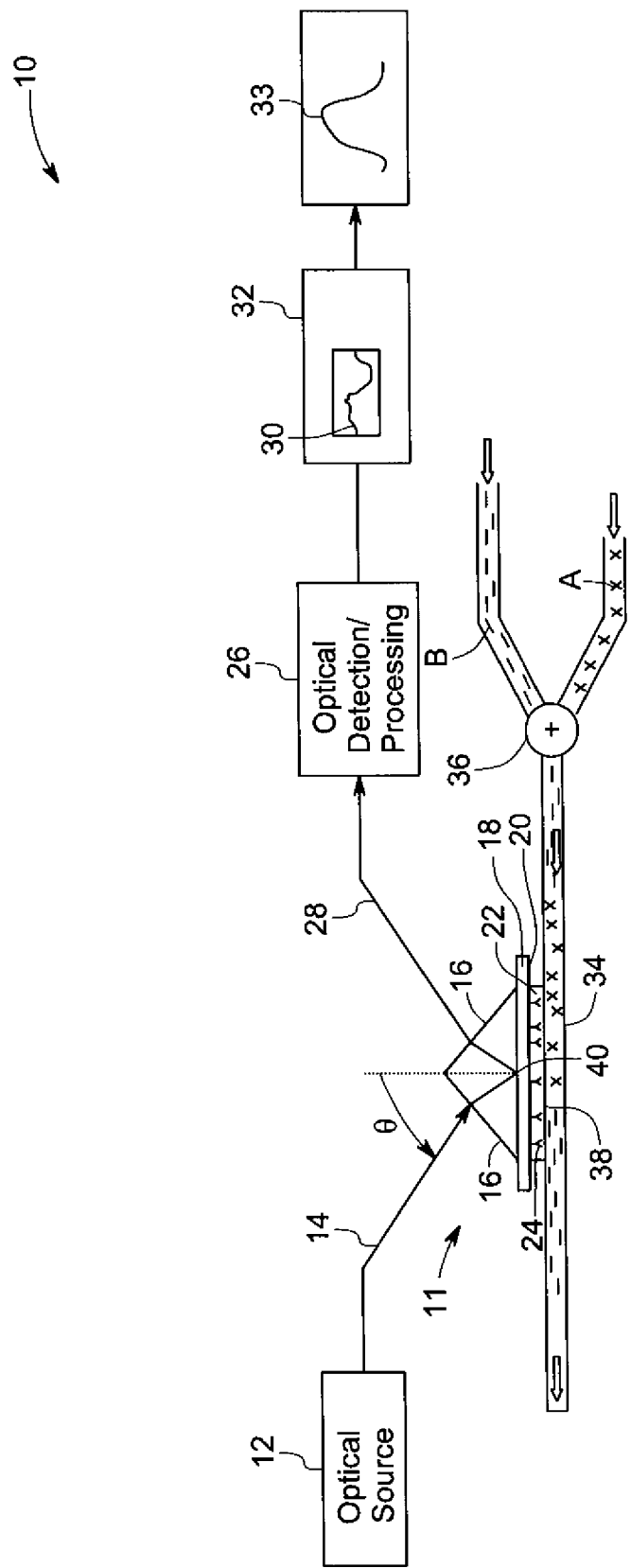
FIG. 1 illustrates a SPR measurement apparatus in accordance with an exemplary embodiment of the invention.

FIG. 1 illustrates an exemplary linear filtering system 10 employed in a SPR measurement apparatus 11. The apparatus 11 is a conventional SPR measurement apparatus for generating a sensorgram. The SPR measurement apparatus 11 includes an optical source 12 that provides optical stimuli 14 to a prism 16 at various angles of incidence $\ominus$ relative to the prism 16. In the illustrated embodiment, the SPR measurement apparatus 10 uses angle-based SPR. In another embodiment, the SPR measurement apparatus 10 employs wavelength based SPR in which the optical source 12 provides optical stimuli 14 to the prism 16 using multiple optical wavelengths. The prism 16 further includes a glass slide 18 with a thin optically reflective substrate 20 such as a gold film and a binding layer 22 that includes ligands 24. In one embodiment, the binding layer 22 is a dielectric layer. The apparatus 11 also includes an optical detection-processing unit 26 that intercepts reflected optical signals 28 that are reflected from the prism 16. The reflected optical signals 28 are further processed by the detection-processing unit 26 to provide a SPR sensorgram 30 at an output device 32. The SPR sensorgram is linearly filtered to generate an output signal that represents a filtered SPR sensorgram 33.

Furthermore, the SPR measurement apparatus 10 has a flow channel 34 through which analytes A and buffer B are alternately flowed past the binding layer 22. The flow of the analytes A and buffer B are controlled using a valve 36 coupled to the channel 34. The positions of the prism interface 38 wherein the optical stimuli 14 are incident may be referred to as targets 40. When the optical stimuli 14 are incident on multiple targets 40 in the prism interface 38, multiple SPR sensorgrams 30 can be provided by the SPR measurement apparatus 10, wherein each SPR sensorgram 30 corresponds to a designated one of the multiple targets 40. The detection-processing unit 26 may also include a processor for receiving the SPR sensorgram 30. The processor may be configured to implement the adaptive linear filtering scheme for noise reduction in SPR sensorgrams 30 and provide the filtered SPR sensorgram 33 in the output device 32.

It should be noted that embodiments of the invention are not limited to any particular processor for performing the processing tasks of the invention. The term "processor," as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art.

Features of the SPR sensorgrams 30 depict phases that represent various physical or biochemical events occurring at the prism interface 38. In operation, the phenomenon of surface plasmon resonance occurs when light is reflected off the reflective substrate 20. A fraction of the light energy (optical stimuli 14) incident at a sharply defined angle may interact with delocalized electrons in the reflective substrate 20 such as metal film, thus reducing the reflected light intensity. The precise angle of incidence at which this occurs is determined by the refractive index close to the backside of the metal film, to which target molecules (analytes A) are immobilized and arrested by the ligands 24 in a mobile phase running along the flow channel 34. If binding occurs to the ligands 24 the local refractive index changes, leading to a change in SPR angle, which is monitored in real-time by detecting changes in the intensity of the reflected optical signals 28, producing the sensorgram 30. The rates of change of the SPR signal are analyzed by the detection-processing unit 26 to yield apparent rate constants for the association and dissociation phases of the interaction at the prism interface 38. The ratio of these values gives an apparent equilibrium constant. The size of the change in SPR signal is directly proportional to the analytes being immobilized and thus, may be interpreted in terms of the stoichiometry of the interaction.

The present method may be referred to as a Dynamic Average Algorithm (DAA) and is a sensorgram filtering algorithm that determines filter length depending on features in the sensorgram. The DAA uses an averaging filter with variable filter length to smooth sensorgrams. The raw data is delayed sample delay (SD) seconds, which allows for a symmetric averaging filter. The maximum half filter length is therefore sample delay (SD) seconds. The filter output is the average of surrounding samples with a centre position delayed sample delay (SD) seconds compared to raw sensorgram data.

Figure 2:
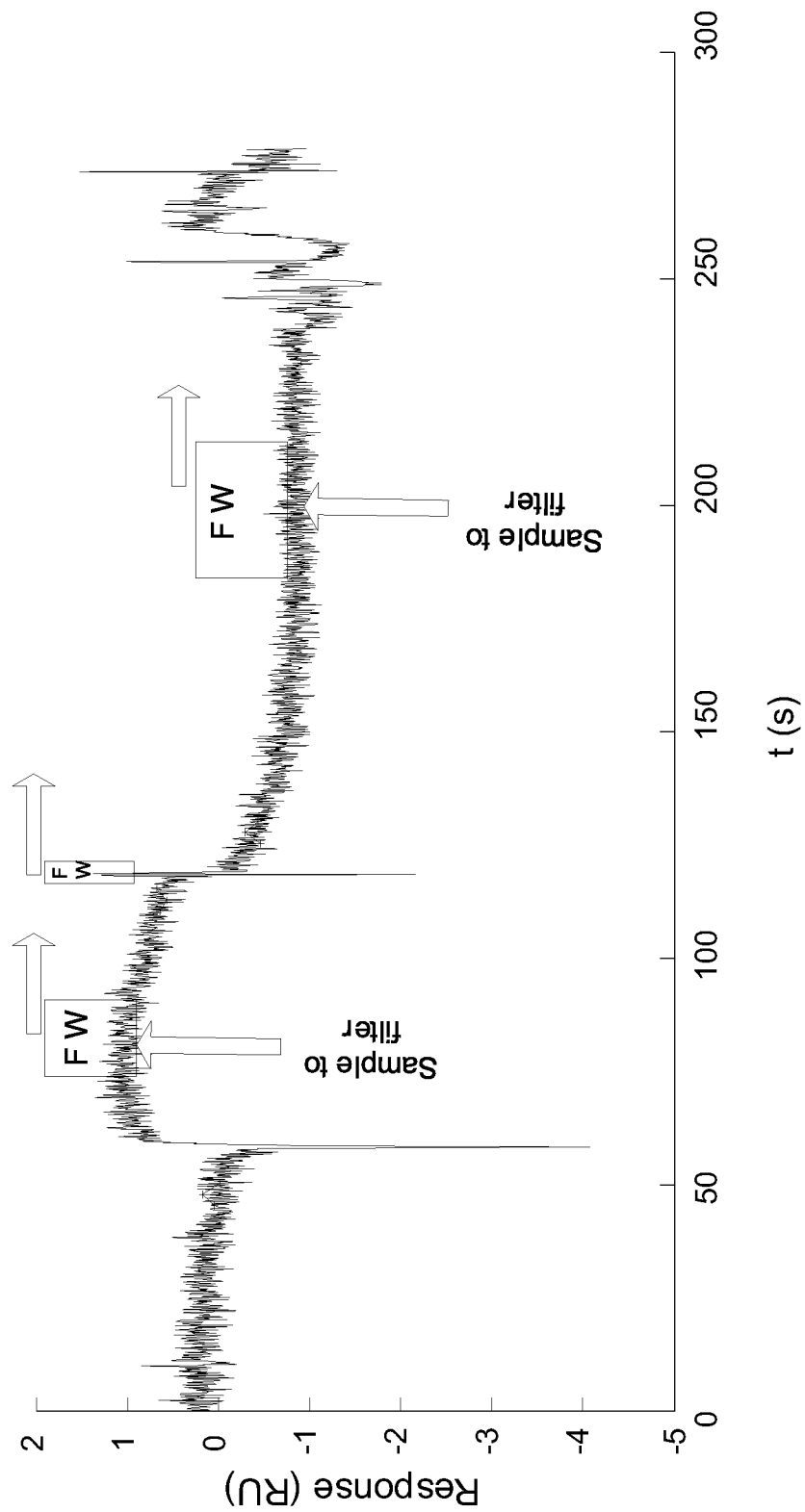
FIG. 2 is an exemplary graphical illustration of a SPR sensorgram illustrating the different filter length modes of the present invention.

The DAA is arranged such that the filter length decreases during fast changing signals and increases during slow changing signals, as is indicated in FIG. 2. Steps and short disturbances (E.g. air bubbles, valve on/off) are regarded as signal while high frequency noise is not regarded as signal and is thus subjet to filtering. According to one embodiment there is provided a method for linear filtering of noise in a sensorgram generated from a surface plasmon resonance apparatus, the method comprising: providing a linear filter of variable length to filter an output signal in the sensorgram; and determining an optimal length of the linear filter based on a slope of the signal in the sensorgram and a locked interception linear error, LILE, detector.

Figure 3:
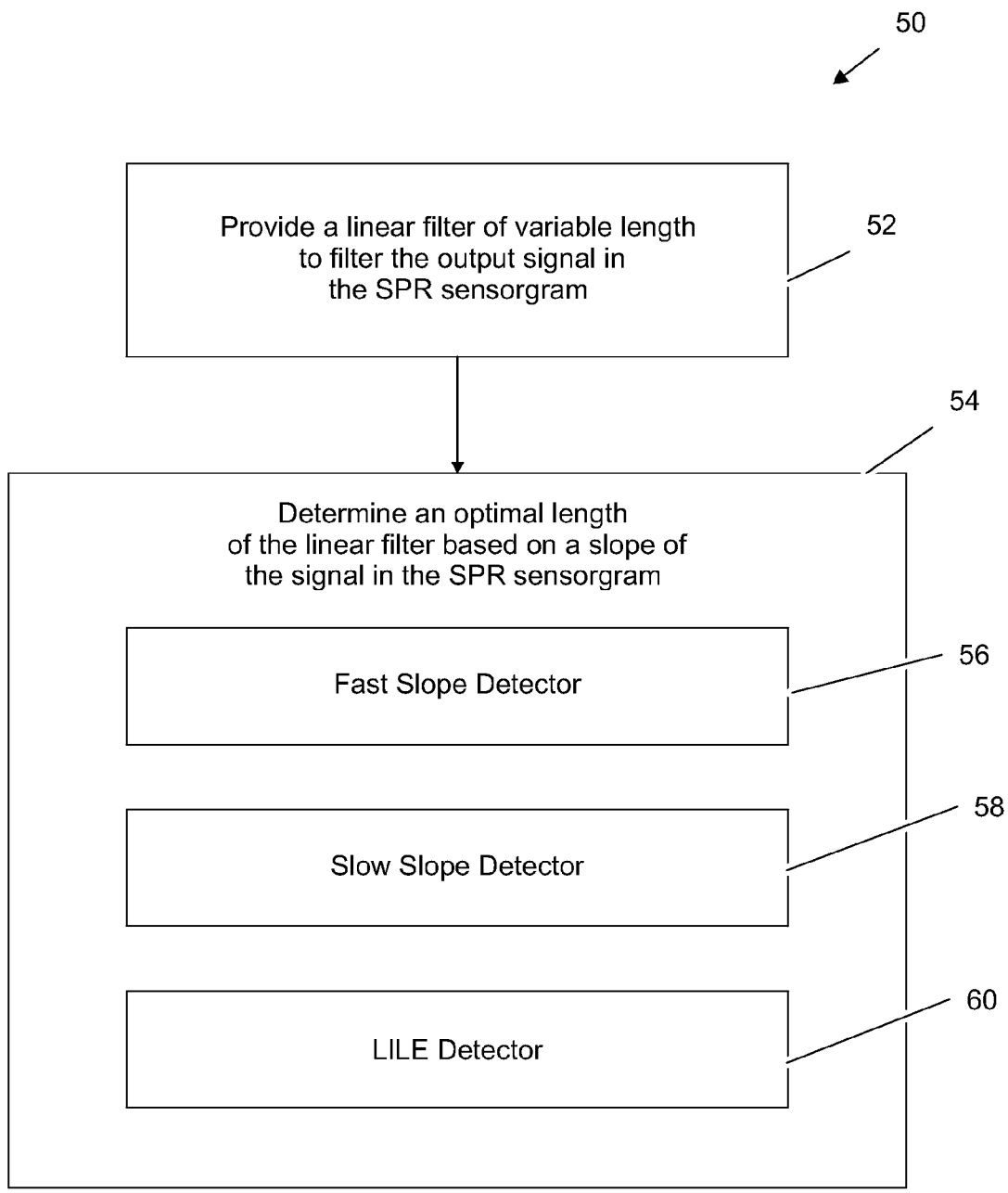
FIG. 3 is a flow chart of a linear filtering method in accordance with an exemplary embodiment of the invention.

FIG. 3 shows a flow chart of a linear filtering method 50 that may employed in FIG. 1. As discussed, the linear filtering method 50 reduces the noise components in the SPR sensorgram but also retains the effectiveness of the SPR signal. This linear filtering method 50 provides for a linear filter of variable length to filter the output signal in the SPR sensorgram at step 52. In one embodiment, the linear filter includes a symmetric finite impulse response (FIR) filter. The symmetric FIR filter length may vary in response to variation of the output signal. In a non-limiting example, the method 50 provides for a long filter length in response to an output signal with decreasing variation. The method 50 also provides for a short filter length in response to an output signal with increasing variation. At step 54, the linear filtering method 50 provides for determining an optimal length of the linear filter based on a slope of the signal in the SPR sensorgram. According to one embodiment, step 54 is performed by a fast slope detector 56, a slow slope detector 58, and a Locked Interception Linear Error, LILE, detector 60. The fast slope detector 56 is arranged to perform calculations to detect fast changes as disturbances and steps in the output signal, whereas the slow slope detector 58 is arranged to perform calculations to detect slow changing signal (e.g. slow and medium kinetics). The LILE detector 60 allows for filtering during high linear slopes, where an average filter does not distort the signal.

All detectors 56, 58, 60 transfer the calculated feature to a specific filter length, FFL, using a threshold and factor in the formula:

$$FFL = SD * e^{-(|feature| - threshold) * factor} \qquad \text{Equation 1}$$

where SD=Sample Delay.

Both slope detectors 56, 58, are calculated as the optimal slope in random noise environment using a linear model for data in a window, see Equation 2 below. The difference is that the fast slope detector 56 has a short window and the slow slope detector 58 has a large window. The parameters that transfer slope to filter length should take into account that a fast slope is more influenced by noise than a slow slope. So the fast slope detector 56 should not detect small and slow slope changes.

The LILE detector 60 is calculated as the Root Mean Square Error (RMSE) of an optimal determined linear curve compared to sensorgram data in a short window based on filter length of the prior iteration. The intercept parameter in the optimal determined linear curve is preferably forced to pass through prior filtered output value to prevent over adjustment to local data. E.g. a high curvature signal will give larger errors in the LILE detector 60 compared to adjusting a linear curve to each window without restrictions. Since the LILE detector 60 gives larger errors for high curvature signals, the filter length will be cautiously increased.

Both slope detector 56, 58 calculations are done as early as possible, e.g. the fast slope detector 56 is calculated earlier than the slow slope detector 58 since it has a smaller window, and ahead of current time for the filtering output. This is possible due to the sample delay SD. The prior filter length+1 (largest possible filter length at this specific time) is used to determine a slope window size. The maximum slope for both the fast- and slow slope detectors 56, 58 are calculated inside the slope window size. The maximum slope is used as the feature parameter in Equation 1.

The filter length is limited to decrease and increase less than or equal to one sample between two samples. Since increasing more than one sample would include more old samples than last time point did.

Each slope detector calculation 56, 58 returns a filter length and the minimum of these two filter lengths and the maximum filter length returned by the LILE detector 60 is utilized to control the average filter length used.

In one embodiment linear filtering method 50, the optimal slope, OS, calculations are performed as:

$$OS = \frac{n\sum xy - \sum x \sum y}{n\sum x^2 - \sum x \sum x}, \quad \text{Equation 2}$$

where n=number of elements, x=time vector and y=response vector.

Figure 4:
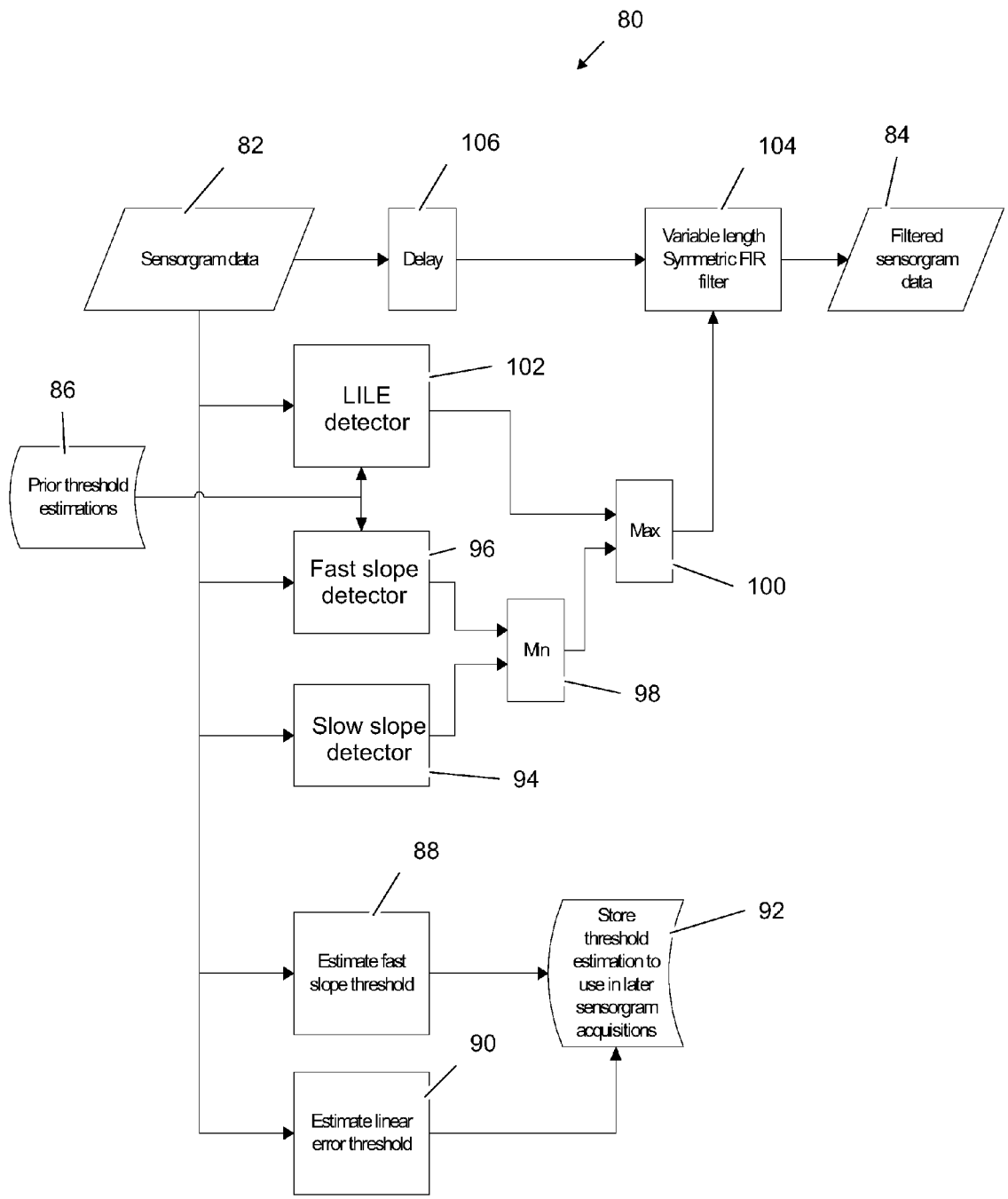
FIG. 4 is a schematic block diagram illustrating a filtering algorithm in accordance with an exemplary embodiment of the invention.

FIG. 4 shows an example of an algorithm iteration process 80, where one input sample 82 gives one filtered output sample 84. One or more input parameters settings 86 are fine tuned for the instrument platform on which the sensogram is acquired. These settings may e.g. be: fast slope threshold (FST), fast slope factor, fast slope window length (FSWL), slow slope threshold, slow slope factor, slow slope window length (SSWL), LILE threshold (LILET), LILE factor, LILE maximum filter length. According to one embodiment FST 88 and LILET 90 are automatically updated during filtering and stored as threshold estimations to be used in later sensogram acquisitions 92, e.g. in Prior threshold parameters 86 for the next cycle. The output filter length from the slow slope 94 and the fast slope detectors 96 are compared at min comparator 98. The shortest filter length is forwarded to the max. comparator 100 where it is compared with the output filter length from the LILE detector 102 and the longest filter length is forwarded to the variable length linear filter 104. Delay module 106 is arranged to delay the sensogram data 82 by e.g. a sample delay SD in order for the slope detectors 94, 96, 102 to calculate the filter length to be used.

According to one embodiment, the iteration process comprises the following steps:

Insert input sample in the beginning of a sample buffer, SB, of length 2*SD. Sample age will increase with increasing buffer index.

Calculate fast slope, FS, using Equation 2 with a small n determined by FSWL

Store FS in a fast slope buffer, FSB.

Calculate slow slope, SS, using Equation 2 with a large n determined by SSWL

Store SS in a slow slope buffer, SSB.

Define a possible filter length to use, PFL=prior iteration filter length+1

Calculate maximum fast slope, MFS, using FSB in a time window determined by PFL and a time position corresponding to input sample time+SD.

Calculate maximum slow slope, MSS, using SSB in a time window determined by PFL and a time position corresponding to input sample time+SD.

Define y vector for LILE calculations, LILEY=SB(SD±LSBW), where LSBW is determined as min(PFL, LILE maximum filter length). Define LILEX as a vector=1 to 2*LSBW Calculate slope, LILES, for LILE calculation using Equation 2 and a LILEY Calculate locked intercept, LILEI=prior filtered output−LILES*prior filtered output sample time Calculate RMSE of linear error, $$LILE = \sqrt{\frac{\sum_{1}^{n} \text{error}^2}{n}},$$

where $\text{error}_i = LILEY_i - (LILES_i * LILEX_i + LILEI_i)$

Calculate fast slope filter length, FSFL, using MFS as feature in Equation 1. The threshold in Equation 1 is FST and is automatically updated according to the module for estimation of thresholds.

Calculate slow slope filter length, SSFL, using MSS as feature in Equation 1

Calculate LILE filter length, LILEFL, using LILE as feature in Equation 1. The threshold in Equation 1 is LILET and is automatically updated according to the module for estimation of thresholds.

Calculate wanted filter length WFL=max(LILEFL,min(FSFL,SSFL))

Set filter length, FL=prior iteration FL+1 if WFL≥prior iteration FL+1

Set filter length, FL=prior iteration FL−1 if WFL≤prior iteration FL−1

Calculate filter output as average of SB(SD±FL)

According to one embodiment, there is provided estimation of thresholds 90 wherein, adjustment to different instruments with different noise level may be done by automatically updating some thresholds during filtering. The goal is to calculate thresholds with minimum effect from outliers. This algorithm is applicable for all threshold calculations. "Feature" in the algorithm can be either LILE or fast slope.

Calculate possible threshold: PT=max(|Feature(TM)|), where TM is a non overlapping time frame in the sensorgram data curve, E.g. 10 seconds of data.

Add PT to an array of curve thresholds, CTA, if PT<X*prior feature threshold. Where X is determined so that outliers will be excluded.

When sensorgram curve data is finished, calculate curve threshold, CT=median(CTA)

Add CT to an array of thresholds, TA, if CT<X*prior feature threshold

Calculate feature threshold=median(TA). Use the feature threshold in the iteration process.

Advantageously, the various embodiments of the invention provide noise reduction in SPR sensorgrams. Thus, the linear filtering method employs a dynamic filtering scheme that not only reduces or eliminates noises but also preserves the SPR signals in the sensorgrams so that the SPR sensorgram is substantially capable of highlighting features, which are indicative of critical biochemical process or event such as the onset of a binding event between analytes and ligands within a sample. Furthermore, the use of a symmetric FIR filter eliminates the possibility of phase distortion that other linear or nonlinear filters may introduce.

Furthermore, the skilled artisan will recognize the interchangeability of various features from different embodiments. For example, the adaptive filter of a linear filtering method can be generated in real-time and based either only on event timings or slopes exclusively. Similarly, the various method steps and features described, as well as other known equivalents for each such methods and feature, can be mixed and matched by one of ordinary skill in this art to construct additional systems and techniques in accordance with principles of this disclosure.

Of course, it is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A processor-implemented method for linear filtering of noise in a sensorgram generated from a surface plasmon resonance apparatus, the method comprising:
   generating and receiving a sensorgram from a surface plasmon resonance measurement apparatus;
   providing a linear filter of variable length to filter an output signal in the sensorgram;
   determining an optimal length of the linear filter based on a first optimal length of the linear filter based on a slope of the signal in the sensorgram and a second optimal length of the linear filter based on a locked interception linear error, LILE, detector, wherein the LILE detector is the Root Mean Square Error (RMSE) of an optimal determined linear curve compared to sensorgram data in a short window based on filter length of a prior iteration process, and wherein an intercept parameter in the optimal determined linear curve is forced to pass through prior filtered output values;
   applying the linear filter to the output signal in the sensorgram to generate a filtered sensorgram; and
   providing the filtered sensorgram to an output device.

2. The method of claim 1, wherein the linear filter provided comprises a symmetric finite impulse response filter.

3. The method of claim 1, wherein the linear filter provided comprises a variable-length symmetric moving average filter.

4. The method of claim 1, wherein the filter length varies dynamically for ensuring the signal in the sensorgram to preserve characteristics indicative of a critical biochemical process.

5. The method of claim 1, further determining a longer filter length when variations in the signal decreases.

6. The method of claim 1, further determining a shorter filter length when variations in the signal increases.

7. The method of claim 1, wherein determining an optimal length of the linear filter based on a slope of the signal in the sensorgram is performed by a fast slope detector and a slow slope detector, and wherein the optimal length of the linear filter based on the slope is selected as the shortest filter length provided by the slope detectors.

8. The method of claim 7, wherein the optimal length of the linear filter is selected as the longest filter length of the optimal length of the linear filter based on the slope and the optimal length of the linear filter based on the LILE detector.

9. A processor-implemented method for linear filtering of noise in a sensorgram generated from a surface plasmon resonance apparatus, the method comprising:
   generating and receiving a sensorgram from a surface plasmon resonance measurement apparatus;
   providing a linear filter of variable length to filter an output signal in the sensorgram;
   determining a first filter length based on a locked interception linear error, LILE, detector, wherein the LLE detector is the Root Mean Square Error (RMSE) of an optimal determined linear curve compared to sensorgram data in a short window based on filter length of a prior iteration process, and wherein an intercept parameter in the optimal determined linear curve is forced to pass through prior filtered output values;
   determining a second filter length based on a slope of the signal between a plurality of events, wherein the plurality of events comprises a fast slope detector detecting fast changes including disturbances or steps in the signal, and a slow slope detector detecting slow changing signals of slow and medium kinetics;
   comparing the first filter length and the second filter length;
   selecting the longer length of either the first filter length or the second filter length;
   applying the linear filter to the output signal in the sensorgram to generate a filtered sensorgram; and
   providing the filtered sensorgram to an output device.

10. The method of claim 9, further providing the second filter length based on an instantaneous slope of the signal.

11. The method of claim 9, further providing a filtering algorithm based on real-time characteristics wherein an output is delayed by a specified amount.

12. The method of claim 9, wherein the fast slope detector has a first window of a first length, and the slow slope detector has a second window of a second length, wherein the first length is shorter than the second length.

13. The method of claim 7, wherein the fast slope detector has a first window of a first length, and the slow slope detector has a second window of a second length, wherein the first length is shorter than the second length.

14. A surface plasmon resonance apparatus, comprising:
   a surface plasmon resonance measurement apparatus configured to generate a sensorgram; and
   a processing unit configured to:
   receive the sensorgram:
   provide a linear filter of a variable length for linear filtering of noise in the sensorgram;
   determine a first filter length based on a locked interception linear error, LILE, detector, wherein the LILE detector is the Root Mean Square Error (RMSE) of an optimal determined linear curve compared to sensorgram data in a short window based on filter length of a prior iteration process, and wherein an intercept parameter in the optimal determined linear curve is forced to pass through prior filtered output values;
   determine a second filter length based on a slope of the signal between a plurality of events, wherein the plurality of events comprises a fast slope detector detecting fast changes including disturbances of steps in the signal, and a slow slope detector detecting slow changing signals of slow and medium kinetics;
   compare the first filter length and the second filter length; and
   select the longer length of either the first filter length or the second filter length;
   apply the linear filter to the sensorgram to generate a filtered sensorgram; and
   provide the filtered sensorgram to an output device.

15. The apparatus of claim 14, wherein the linear filter provided comprises a symmetric finite impulse response filter.

16. The apparatus of claim 14, wherein the linear filter provided comprises a variable-length symmetric moving average filter.

17. The apparatus of claim 14, wherein the filter length varies dynamically for ensuring the signal in the sensorgram to preserve characteristics indicative of a critical biochemical process.

18. The apparatus of claim 14, further determining a longer filter length when variations in the signal decreases.

19. The apparatus of claim 14, further determining a shorter filter length when variations in the signal increases.

20. The apparatus of claim 14, wherein the fast slope detector has a first window of a first length, and the slow slope detector has a second window of a second length, wherein the first length is shorter than the second length.

\* \* \* \* \*